(12) United States Patent
Connell, II (10) Patent No.: US 7,810,926 B2
(45) Date of Patent: Oct. 12, 2010

(54) LATERAL GAZE ANGLE ESTIMATION USING RELATIVE EYE SEPARATION

(75) Inventor: Jonathan H. Connell, II, Cortlandt-Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 49 days.

(21) Appl. No.: 12/371,606

(22) Filed: Feb. 15, 2009

(65) Prior Publication Data

US 2010/0208206 A1    Aug. 19, 2010

(51) Int. Cl.
*A61B 3/14* (2006.01)
(52) U.S. Cl. .................... 351/210; 351/204; 351/246
(58) Field of Classification Search ................ 351/200, 351/204, 205, 209, 210, 246
See application file for complete search history.

(56) References Cited

U.S. PATENT DOCUMENTS

| 5,155,516 A | 10/1992 | Shindo |
|---|---|---|
| 5,293,535 A | 3/1994 | Sensui |
| 5,428,413 A | 6/1995 | Shindo |
| 5,557,364 A | 9/1996 | Shindo et al. |
| 5,561,973 A | 10/1996 | St. Germain |
| 5,608,489 A | 3/1997 | Ozaki |
| 6,152,563 A | 11/2000 | Hutchinson et al. |
| 6,331,168 B1 | 12/2001 | Socci et al. |
| 7,306,337 B2 * | 12/2007 | Ji et al. ................ 351/209 |
| 7,458,901 B2 | 12/2008 | Hoganson |
| 7,460,940 B2 | 12/2008 | Larsson et al. |
| 2006/0189405 A1 | 8/2006 | Hoganson |
| 2009/0109400 A1 * | 4/2009 | Yoshinaga et al. ........ 351/210 |

* cited by examiner

*Primary Examiner*—Huy K Mai
(74) *Attorney, Agent, or Firm*—Anna L. Linne; Ronald A. D'Alessandro; Keohane & D'Alessandro PLLC (57) ABSTRACT

This invention provides for the automatic determination of a human's gaze angle. The gaze angle is assumed to be the same as the head angle (i.e., eyes looking straight ahead). It is determined by comparing the observed eye separation relative to a maximal eye separation. The gaze angle is then determined to be the inverse cosine, or arc cosine, of the ratio of these two measurements.

20 Claims, 8 Drawing Sheets

LATERAL GAZE ANGLE ESTIMATION USING RELATIVE EYE SEPARATION

FIELD OF THE INVENTION

The present invention provides automatic lateral gaze angle estimation using relative eye separation.

BACKGROUND OF THE INVENTION

There are many applications where detecting when a human user is looking directly at a device is desirable. One such application is self-service kiosks. The kiosk may be in a general attention attracting mode with flashy graphics until someone actually looks at the device. At this point, it may launch a targeted promotion because it has the user's attention.

Kiosk application can be activated by simple proximity sensors or by machine vision systems employing techniques such as background subtraction. However, these solutions only assure that a person is nearby, not that he is looking at the device.

Another application where detecting when a human user is looking directly at a device is desirable is operator alertness monitoring. At regular intervals, in order to operate the vehicle properly, the operator of a machine may be required to look at various task-relevant areas or directions. For instance, an alert driver of a car needs to look forward through the windshield and occasionally at the rearview mirror. If this does not occur, or only one point is being looked at, the driver may have become drowsy. The proper alternation of direct gaze between, e.g., the windshield and the rear-view mirror, may be determined by placing a gaze detector at each special point, e.g., the base of the windshield and in the rearview mirror. One could also put a signaling device, such as a blinking light, in conjunction with the detection camera to deliberately draw the user's attention to the spot if, for instance, the user is not looking in that direction frequently enough.

There are also a number of driver alertness systems. Many of these are based on blink frequency or eyelid closing rate. As such, they do not ensure that a driver is paying attention to the important aspects of his environment (e.g., he may be facing the passenger or text messaging rather than looking straight ahead).

There are other applications where determining the gaze angle of a human subject is important. Clearly, gaze angle of the user's head can be used to infer what the user is looking at as, in general, the user is looking in the direction of where his/her head is pointing. If the configuration of the user's external environment relative to the user is known, "interest" maps may be built if the user's gaze angle may be determined. For instance, as a customer roams down the aisle in a grocery store, a map of interest of the type of groceries that the user is interested in may be built based upon which groceries the user looks at. For instance, if the user gazes towards pasta on one side of the aisle while ignoring another ethnic food group on the other side of the aisle, it may be determined that the user has more interest in the pasta products.

There are some eye-tracking devices on the market. However, many of these eye-tracking devices must be worn by the user. Others are bulky or have a limited range of acceptable positions for the user's head.

There are also many systems that may find human faces in video images, but they are typically limited to nearly frontal views and make no effort to estimate head rotation or gaze direction. Systems that additionally determine head rotation often involve many template convolutions and hence are computationally costly.

Present methods for gaze angle such as a neural net classifier or a dense stereo reconstruction that looks for the nose are computationally complex.

SUMMARY OF THE INVENTION

This invention estimates the gaze angle of the head of a human subject using one or more video cameras. Once determined, the gaze angle may be used to infer what the user is looking at in the user's environment if the configuration of the environment relative to the user is known.

This invention provides for the automatic estimation of a human's gaze angle. The gaze angle is assumed to be the same as the head angle (i.e., eyes looking straight ahead). It is determined by comparing the observed eye separation relative to either a maximal eye separation, or the separation measured from a different vantage point. There is generally a left/right ambiguity to this result that can be resolved by simply identifying the side of the head the eyes are located.

One embodiment discloses a method for lateral gaze angle estimation of a head of a user having two eyes using the determination of relative eye separation of the user, each eye having a pupil region, the method comprising finding the pupil region of each eye of the user in a video camera image from a video camera, measuring an eye separation distance between the substantial centers of the pupil regions, and determining the lateral gaze angle based upon the measured distance.

Another embodiment illustrates a system for lateral gaze angle estimation of a head of a user using the determination of relative eye separation of the user, each eye having a pupil region, the system comprising at least one processing unit, a memory unit operably associated with the at least one processing unit, a lateral gaze determination tool storable in the memory unit and executable by the at least one memory unit, the lateral gaze determination tool comprising a pupil region finding unit of each eye of the user in a video camera image from a video camera, an eye separation distance measuring unit for measuring the separation distance between the substantial centers of the pupil regions, and a lateral gaze angle determining unit based upon the measured distance.

In yet another embodiment, a computer program product is embodied in a computer readable medium for operating in a system comprising a processing unit, a memory, a bus, and input/output (I/O) interfaces, for implementing a method for estimating lateral gaze angle of a head of a user having two eyes using the determination of relative eye separation, each eye having a pupil region, the method comprising finding the pupil region of each eye of the user in a video camera image from a video camera, measuring an eye separation distance between the substantial centers of the pupil regions, and determining the lateral gaze angle based upon the measured distance.

Another embodiment discloses a method for deploying computing infrastructure comprising integrating computer-readable code into a computing system, wherein the code in combination with the computing system is capable of performing a process for lateral gaze angle estimation of a head of a user having two eyes using the determination of relative eye separation of the user, each eye having a pupil region, the process comprising finding the pupil region of each eye of the user in a video camera image from a video camera, measuring an eye separation distance between the substantial centers of the pupil regions, and determining the lateral gaze angle based upon the measured distance.

BRIEF DESCRIPTION OF THE DRAWINGS

These and other features of this invention will be more readily understood from the following detailed description of the various aspects of the invention taken in conjunction with the accompanying drawings in which.

The drawings are not necessarily to scale. The drawings are merely schematic representations, not intended to portray specific parameters of the invention. The drawings are intended to depict only typical embodiments of the invention, and therefore should not be considered as limiting the scope of the invention.

DETAILED DESCRIPTION OF THE INVENTION

The present invention provides automatic lateral gaze angle estimation of a human of interest using relative eye separation.

The present invention may employ one or more standard video cameras, may operate in a non-contact mode, and may have a fairly wide working zone. Also, a complete image analysis is not required; only a method to find the eyes of the human for which the invention is estimating a lateral gaze angle is required. Furthermore, resolving the gaze angle from two measurements is simple computationally.

Figure 1:
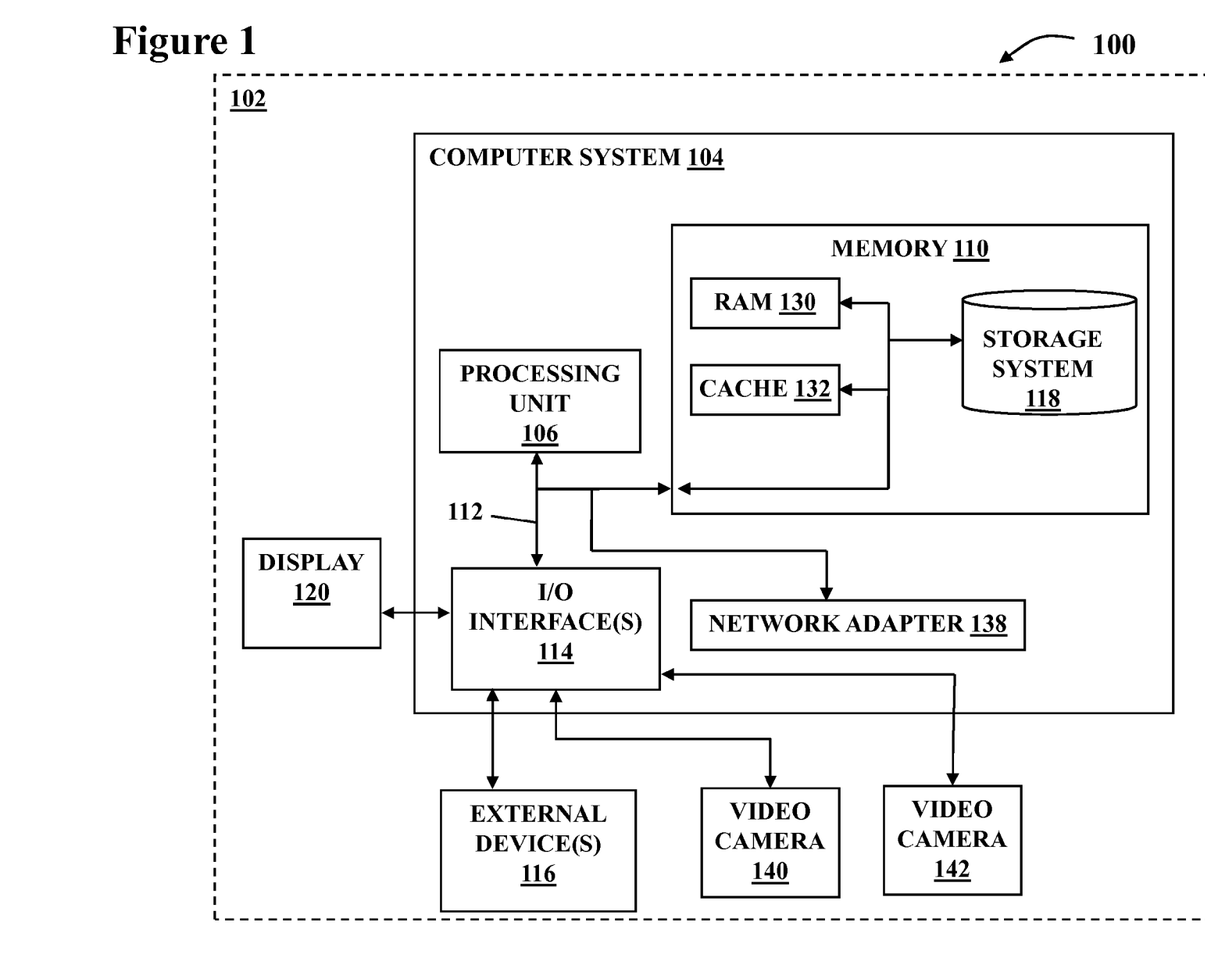
FIG. 1 shows a data processing system suitable for implementing an embodiment of the present invention.

A system, such as system 100, may have a data processing system, such as data processing system 102 shown in FIG. 1, suitable for storing and/or executing program code of the present invention, and may include a computer system, such as computer system 104, having at least one processing unit (processing unit 106) coupled directly or indirectly to memory elements (memory 110) through a system bus, such as system bus 112. Memory 110 may include local memory (RAM 130) employed during actual execution of the program code, bulk storage (storage 118), and cache memories (cache 132) that provide temporary storage of at least some program code in order to reduce the number of times code must be retrieved from storage 118 during execution. Input/output or I/O devices (such as display 120, and other external devices (external devices 116)), including but not limited to keyboards, pointing devices, etc., may be coupled to computer system 104 either directly or through intervening I/O controllers (I/O interface(s) 114). I/O interface(s) 114 may further couple video cameras 140, 142 for finding a user's eyes to computer system 104. Network adapter(s) (network adapter 138) may provide access to external networks.

Figure 2:
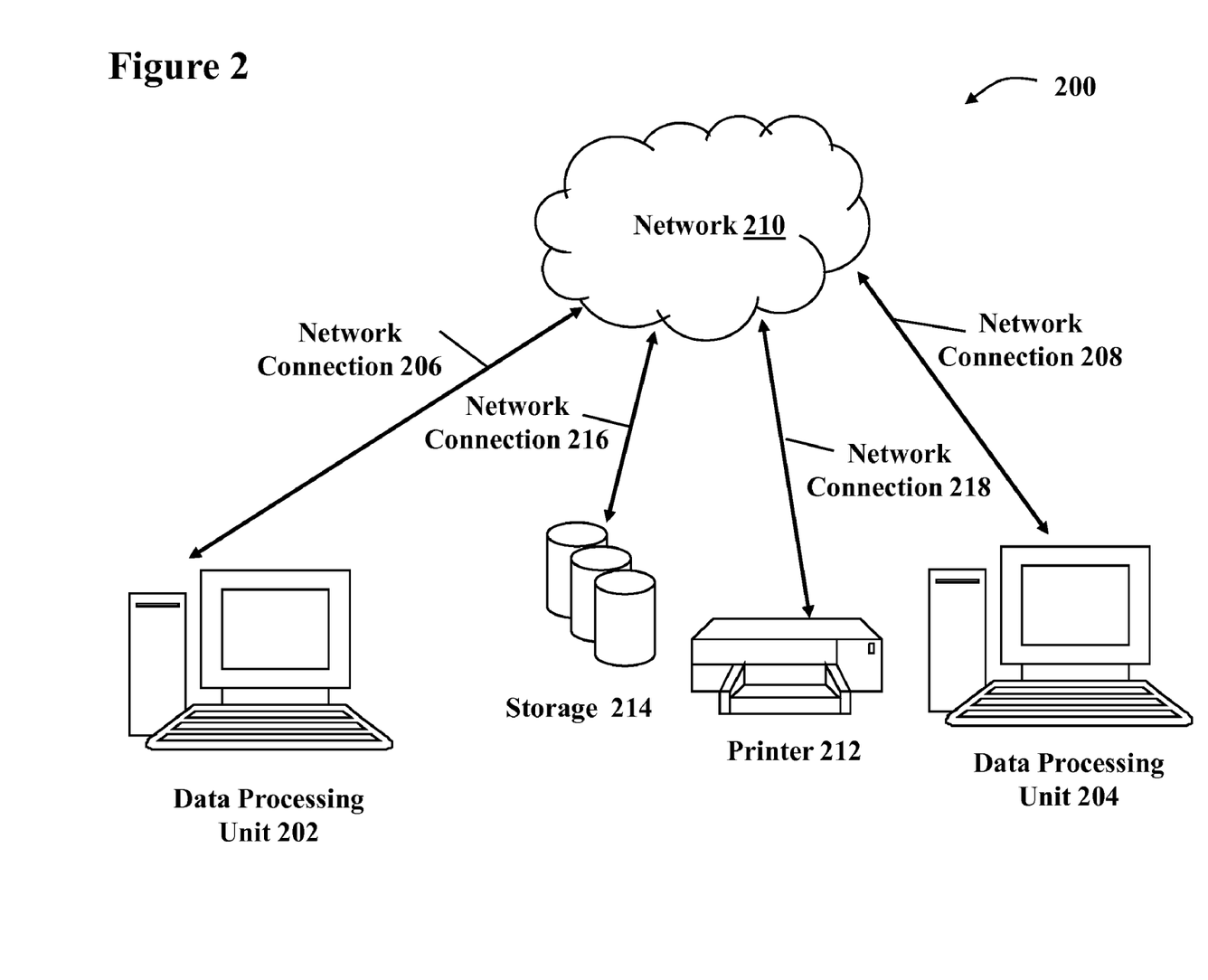
FIG. 2 shows a network for implementing an embodiment of the present invention.

FIG. 2 illustrates a networked system, such as system 200, to enable a data processing system (data processing unit 202) to be coupled through network connection(s) (network connection 206, 208, 216, 218) to other data processing systems (data processing unit 204), remote printers (printer 212) and/or storage devices (storage 214) through intervening private and/or public network(s) (network 210).

The gaze angle of a human of interest is assumed to be the same as the head angle (i.e., eyes looking straight ahead). It is determined by comparing the observed eye separation relative to either a maximal eye separation, or the separation measured from a different vantage point.

Figure 3:
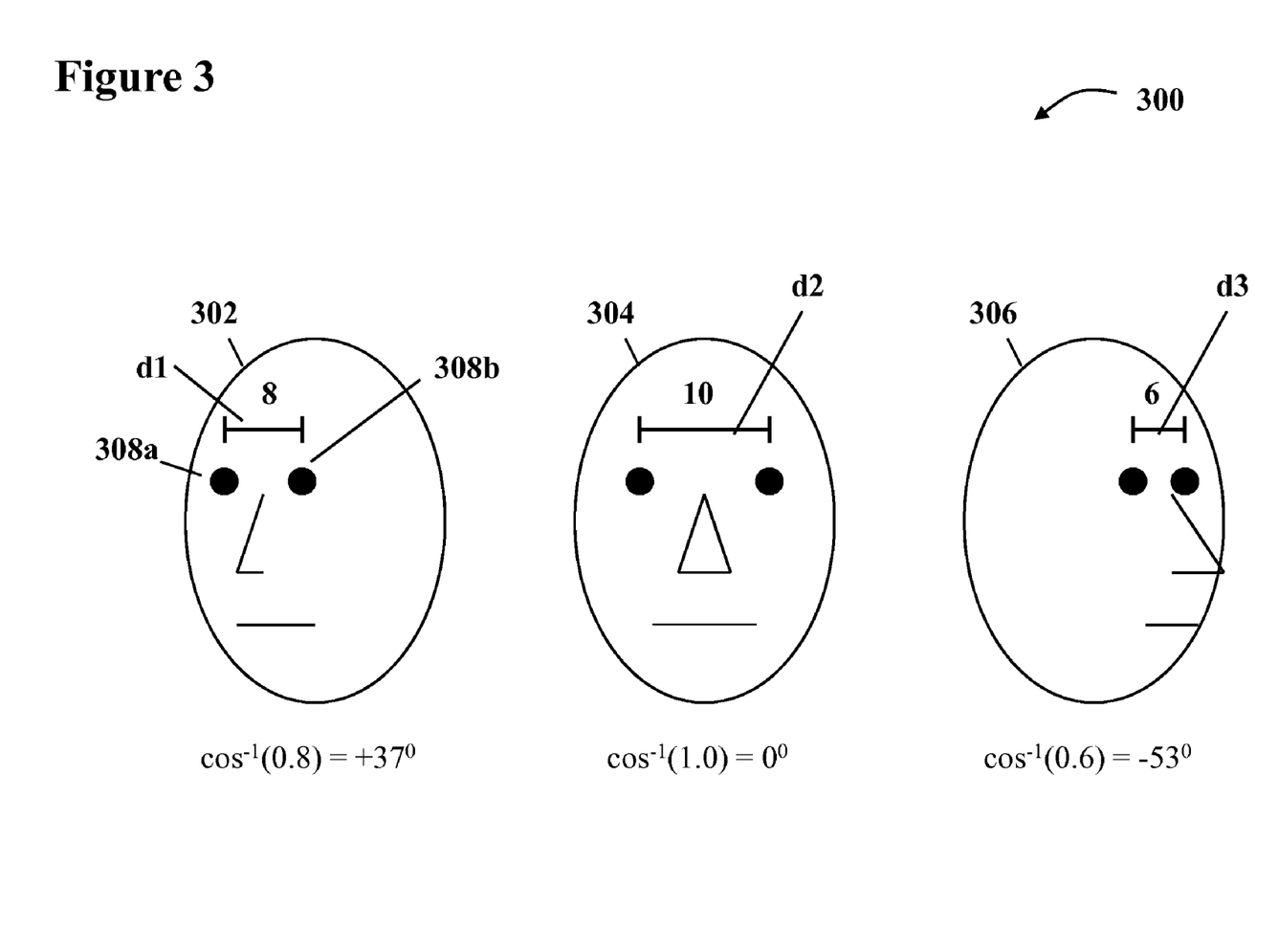
FIG. 3 illustrates various examples of lateral gaze angles having correspondingly different eye separation.

For example, FIG. 3 illustrates three heads: right looking head 302, straight looking head 304, and left looking head 306. Each human head, of course, has two eyes 308a, 308b separated by distance d1, d2, d3. The gaze angle of the head with respect to a fixed location may make the appearance of the distance separating the user's eyes appear closer together from the perspective of the fixed location. For instance, straight looking head 304, that is, looking directly at the point of reference, has the maximal eye separation distance, d2, which is 10 in the example shown in FIG. 3. That is, the eye separation distance for the user cannot appear greater than d2 since the user's head is looking straight ahead at the point of reference. If the user's head is right looking (right looking head 302), that is, having a right lateral gaze angle, relative eye separation distance d1 will be less than the maximal eye separation distance, d2. In the example of FIG. 3, relative eye separation distance d1 is 8. If the user's head is left looking (left looking head 306), that is, having a left lateral gaze angle, eye separation distance d3 will be less than the maximal eye separation distance, d2. In the example of FIG. 3, relative eye separation distance d3 is 6.

A video camera, such as video camera 140 and/or video camera 142, locates the human eyes and pupils (or pupil regions) of the human face of interest and measures the distance between the eyes by counting the pixel distance between their centers in the image. Once the measurement has been taken, the measurement is run through the formula of $\cos^{-1}$ (ratio of measurement and maximal value (10 in the example of FIG. 3)). The result is used by the system to estimate the lateral gaze angle estimation using relative eye separation. As shown in the calculations of FIG. 3, straight looking head 304 has a lateral gaze angle of arccos (1.0), or 0 degrees. Right looking head 302 has a lateral gaze angle of arccos (0.8), or +37 degrees. Left looking head 306 has a lateral gaze angle of arccos (0.6), or −53 degrees.

Figure 4:
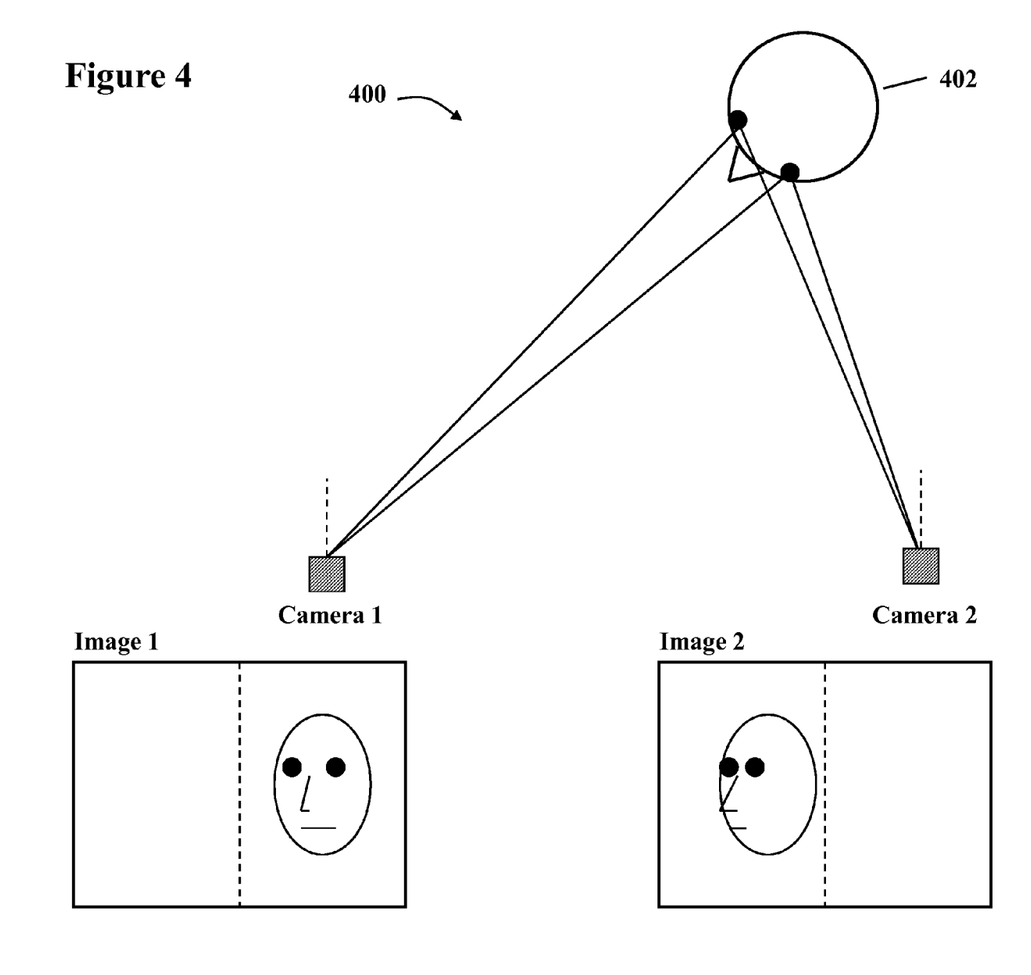
FIG. 4 illustrates one embodiment of a system of the present invention having two cameras for identifying the gaze angle of a human of interest.

Another technique that can be used to determine lateral gaze is shown in FIG. 4 showing system 400 having camera 1 and camera 2. Camera 1 and camera 2 each detect each eye and pupil or pupil region 410, 412 of a head 402. Camera 1 acquires image 1 from its viewing angle. The technique is to obtain the second image (image 2 by camera 2) at a known angular offset relative to the view of camera 2. The eye separation in the two views can then be compared to generate an estimate of the gaze angle. The separation of camera 1, camera 2 is known as is the relative orientation of their optical axes (dotted lines). One way to solve the head orientation position is to apply triangulation to determine the position of each eye in space. This is possible because the image coordinates of the detected eye can be turned into a ray at a particular angle provided that the intrinsic parameters of the camera lens are known. Using triangulation between the rays from the two cameras the actual position of each eye in space can be found. The angle of the line connecting the two eyes relative to the viewing direction of camera 1 can then be computed directly. However, this method may be prone to range estimation errors that get magnified when determining the gaze angle.

Another technique for estimating lateral gaze angle is to compute the shift of view direction between the two cameras for the eye centers. This is the apex angle of the triangle formed by the center of the eye pair and the two cameras. Assuming the camera separation is B (base of triangle) and the observed center angles are C1 and C2 (between the base and the sides of the triangles). The relative viewing angle shift A=180−C1−C2 (in degrees). The distances D1 and D2 from each camera to the center point (legs of the triangle) can also be computed using B, C1, and C2. This can be combined with the eye separations S1 and S2 observed in the two cameras to give the gaze angle relative to the center point. Let S2'=S2*D1/D2 to adjust for the magnification due to different distances. Equations $51=E*\cos(G)$ and $S2'=E*\cos(G+A)$ where G is the gaze angle relative to Camera 1 and E is the true separation of the eyes. Solving for E and substituting (i.e., the value of E does not need to known), constraint equation $S2'*\cos(G)=S1*\cos(G+A)$ is arrived at. This can be solved for $G=\arctan[(S1*\cos(A)−S2')/(S1*\sin(A))]$. Comparing the observed eye separations in this way is less sensitive to parallax errors than the direct stereo method.

Typically, the system first needs to find the pupil regions in the video image captured by video camera. A quick, simple, and reliable way to do this is to utilize the "red-eye" effect. The red-eye effect is the common appearance of red pupils in color photographs of eyes. It occurs when using a photographic flash very close to the camera lens, in ambient low light. Because the light of the flash occurs too fast for the pupil to close, much of the very bright light from the flash passes into the eye through the pupil, reflects off the fundus at the back of the eyeball, and out through the pupil. The camera records this reflected light. The red-eye effect is due to the color of the fundus, which is due to melanin, a pigment, principally located in the retinal pigment epithelium (RPE).

Figure 5:
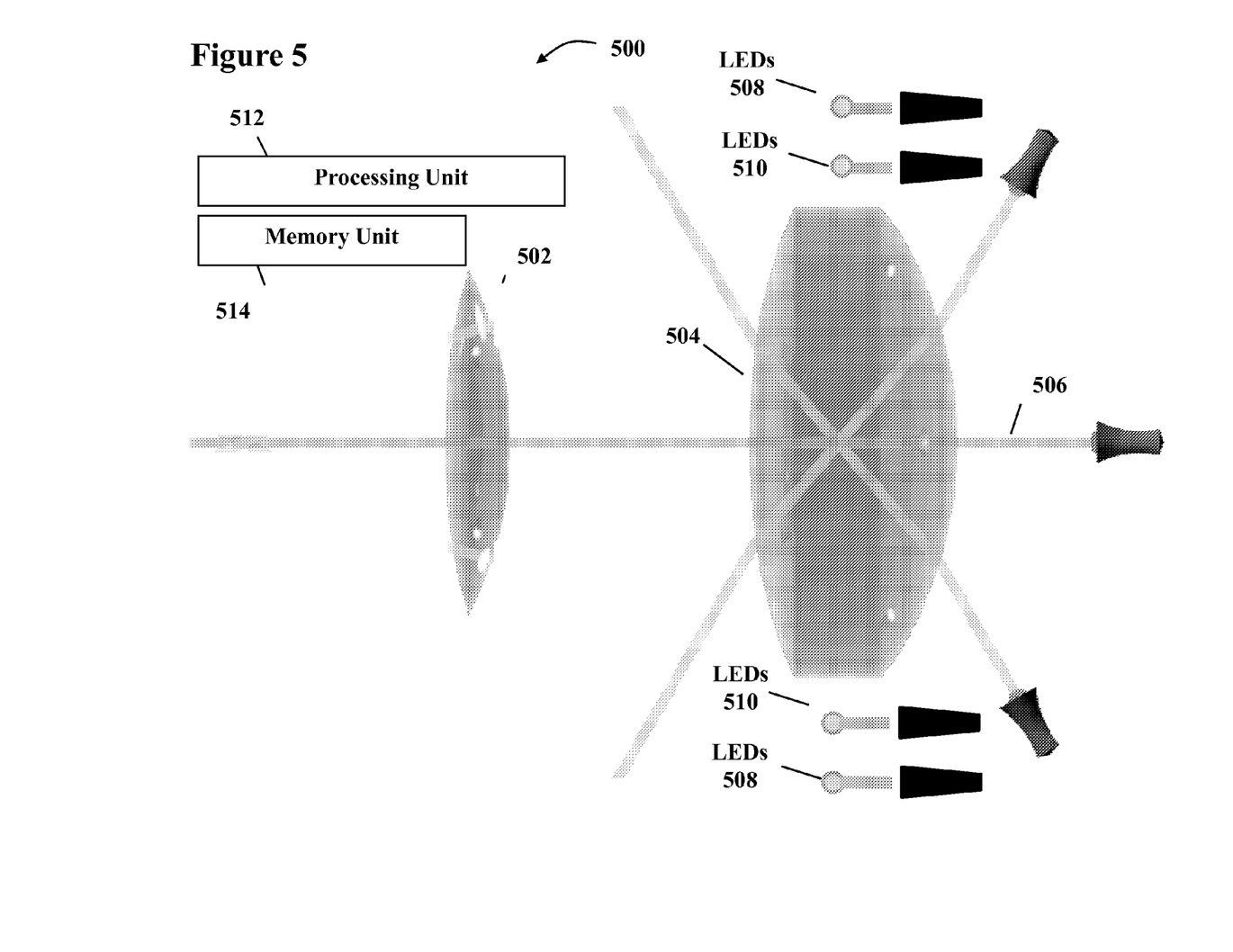
FIG. 5 illustrates an embodiment of the present invention having lenses, two rings of LEDs, and an optical axis.

As shown in FIG. 5, a ring of near-infrared light-emitting diodes (LEDs 508) are positioned around the camera lens and positioned near optical axis 506 of camera. LEDs 508 are flashed on and an image of the environment is acquired. (In optics, the term optical axis is used to define a direction along which there is some degree of rotational symmetry. It can be used in several contexts. In an optical system, the optical axis is an imaginary line that defines the path along which light propagates through the system. For a system composed of simple lenses (such as lenses 502, 504) and mirrors, the axis passes through the center of curvature of each surface, and coincides with the axis of rotational symmetry. The optical axis is often coincident with the system's mechanical axis, but not always, as in the case of off-axis optical systems.)

Figure 6:
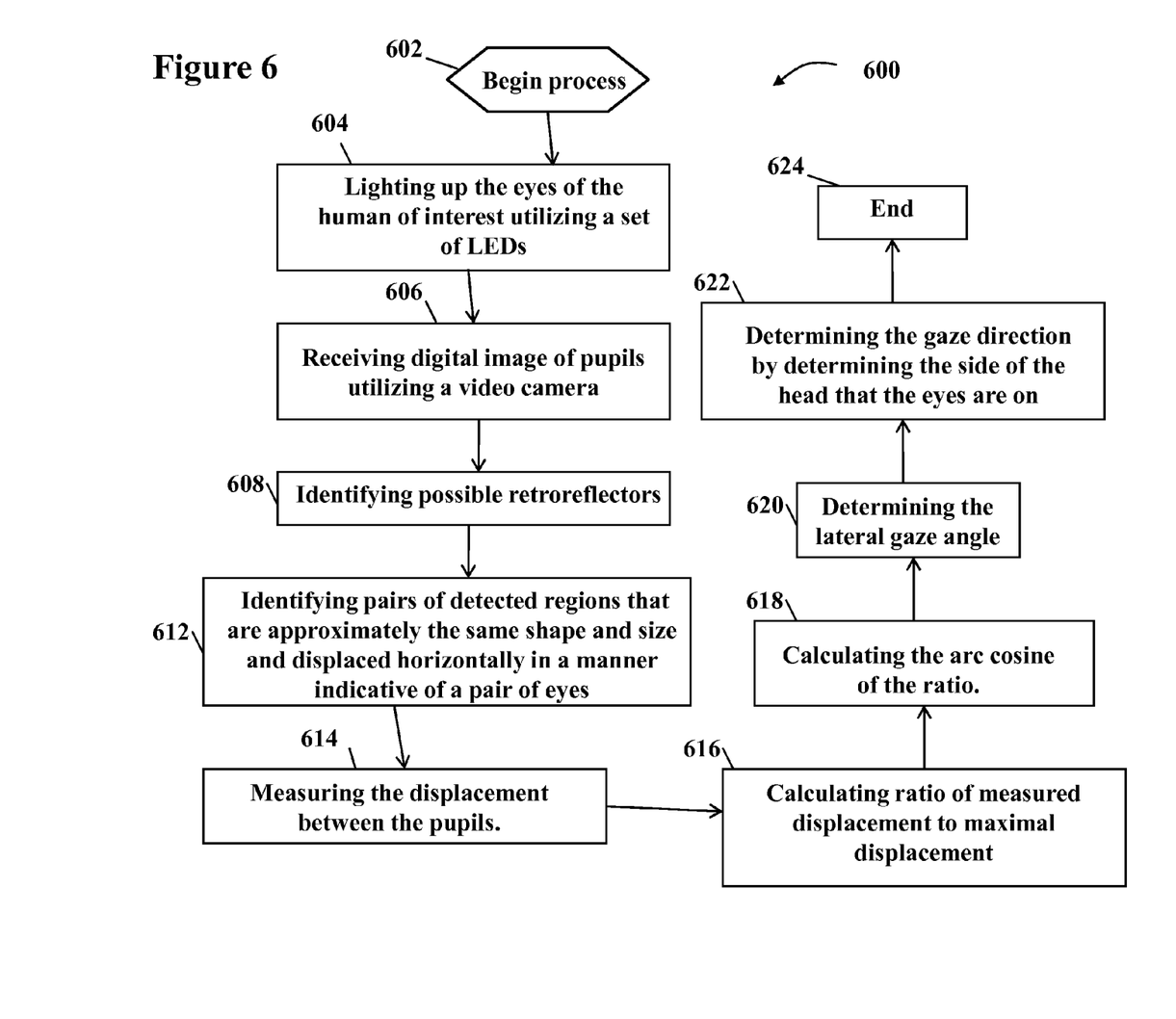
FIG. 6 illustrates one embodiment of a method for scanning a user's eyes and pupil regions and for determining whether the user is looking at the video camera.

This is shown in method 600 in FIG. 6 which begins at 602 and continues to 604. At 606, another image is then acquired with a similar ring of LEDs (LEDs 510) further displaced from optical axis 506 of camera system 140. (In optics, the term optical axis is used to define a direction along which there is some degree of rotational symmetry. In an optical system, the optical axis is an imaginary line that defines the path along which light propagates through the system.) This is shown as 506 in FIG. 5 in system 500. For a system composed of simple lenses (lens 502, lens 504) and mirrors, optical axis 506 passes through the center of curvature of each surface, and coincides with the axis of rotational symmetry. The optical axis is often coincident with the system's mechanical axis, but not always, as in the case of off-axis optical systems.

At 608 of FIG. 6, possible retroreflectors are identified. (A retroreflector (sometimes called a retroflector) is a device or surface that reflects light back to its source with a minimum scattering of light. A human eye can be considered to be a retroreflector.) Next, at 612, the system identifies pairs of detected regions that are approximately the same shape and size and displaced horizontally in a manner indicative of a pair of eyes. At 614, the displacement between the pupil pairs are measured.

Alternatively, the eyes might be found by template matching to a model eye(s) or by looking for time differences in a video stream that are induced by eye blink motions.

To resolve the left/right ambiguity it helps if the system can determine whether the center of the eye pair is to the left or right of the center of the head region (separately detected). However, if the intent is to only recognize a direct gaze then this step is not needed—the user is looking directly at the camera when the eye separation is close to the maximum that has ever been observed (e.g., a separation within 2% of max means gaze is +/−11 degrees of direct).

Figure 7:
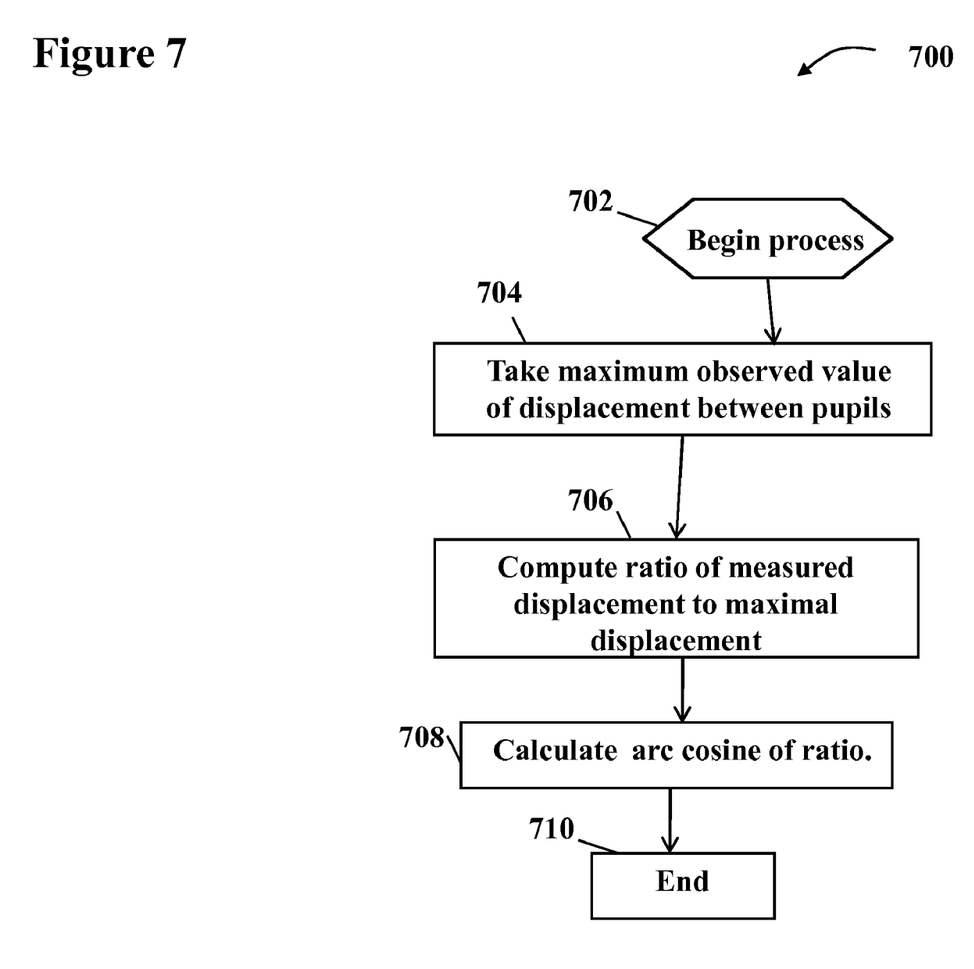
FIG. 7 illustrates one embodiment of the method of the present invention for determining the lateral gaze angle of a user's head based upon the observed separation of the user's eyes with respect to the camera's angle

One way of obtaining a maximal eye separation is to take the maximum observed value over a time interval at 704 is shown in method 700 of FIG. 7 which starts at 702. The currently observed separation is then compared to this maximum value at 706 and the arc-cosine computed to derive the gaze angle at 708. This technique is effective if the user's head stays at approximately the same distance (i.e., minimal looming from perspective) and the user actively gazes from side to side (including straight forward at some point).

Figure 8:
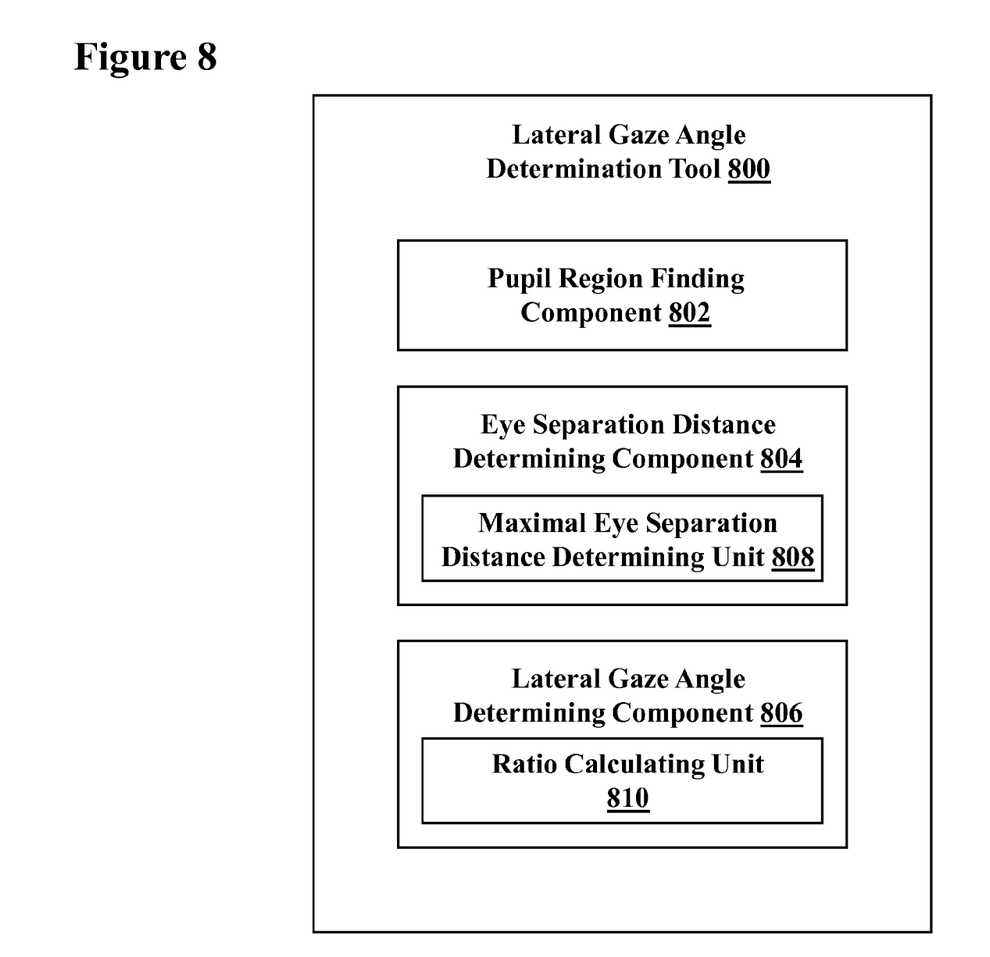
FIG. 8 illustrates an embodiment of a lateral gaze estimation tool of the present invention.

FIG. 8 illustrates a lateral gaze angle determination tool 800 for being implemented within memory 514 utilizing processing unit 512. Lateral gaze angle determination tool 800 has pupil finding component 802 that performs the function of finding the pupils of the human of interest. Tool 800 further has eye separation distance determining component 804 for determining the distance between the eyes of the human of interest as found by pupil finding component 802. Eye separation distance determining component 804 has maximal eye separation distance determining unit 808 for determining an approximate maximal eye separation distance between the eyes of a "standard" human. Maximal eye separation distance determining unit 808 may be configured for recording multiple measured eye separation distances over a period of time and determining the maximal eye separation distance by identifying the maximum measured eye separation distance from the multiple measured eye separation distances. Lateral gaze angle determining component 806 performs the function of determining the lateral gaze angle from the information received from eye separation distance determining component 804. Lateral gaze angle determining component 806 has ratio calculating unit 810 for calculating the ratio of the measured eye separation distance to the maximal eye separation distance and calculating an inverse cosine value of the ratio. Lateral gaze angle determining component 806 may be configured to calculate the lateral gaze angle based upon the calculated inverse cosine value.

It should be understood that the present invention is typically computer-implemented via hardware and/or software. As such, and client systems and/or servers will include computerized components as known in the art. Such components typically include (among others), a processing unit, a memory, a bus, input/output (I/O) interfaces, external devices, etc. It should also be understood that although a specific embodiment providing lateral gaze angle estimation using relative eye separation of a user has been depicted and described, the present invention could be implemented in conjunction with any type of system where lateral gaze angle estimation is desirable.

While shown and described herein is a system and method for lateral gaze angle estimation using relative eye separation of a user, it is understood that the invention further provides various alternative embodiments. For example, in one embodiment, the invention provides a computer-readable/useable medium that includes computer program code to enable a computer infrastructure to provide lateral gaze angle estimation using relative eye separation of a user. To this extent, the computer-readable/useable medium includes program code that implements each of the various process steps of the invention. It is understood that the terms computer-readable medium or computer useable medium comprises one or more of any type of physical embodiment of the program code. In particular, the computer-readable/useable medium can comprise program code embodied on one or more portable storage articles of manufacture (e.g., a compact disc, a magnetic disk, a tape, etc.), on one or more data storage portions of a computing device, such as memory and/or storage system (e.g., a fixed disk, a read-only memory, a random access memory, a cache memory, etc.), and/or as a data signal (e.g., a propagated signal) traveling over a network (e.g., during a wired/wireless electronic distribution of the program code).

In another embodiment, the invention provides a computer-implemented method for lateral gaze angle estimation using relative eye separation of a user. In this case, a computerized infrastructure can be provided and one or more systems for performing the process steps of the invention can be obtained (e.g., created, purchased, used, modified, etc.) and deployed to the computerized infrastructure. To this extent, the deployment of a system can comprise one or more of (1) installing program code on a computing device, such as computer system from a computer-readable medium; (2) adding one or more computing devices to the computer infrastructure; and (3) incorporating and/or modifying one or more existing systems of the computer infrastructure to enable the computerized infrastructure to perform the process steps of the invention.

As used herein, it is understood that the terms "program code" and "computer program code" are synonymous and mean any expression, in any language, code or notation, of a set of instructions intended to cause a computing device having an information processing capability to perform a particular function either directly or after either or both of the following: (a) conversion to another language, code or notation; and/or (b) reproduction in a different material form. To this extent, program code can be embodied as one or more of: an application/software program, component software/a library of functions, an operating system, a basic I/O system/driver for a particular computing and/or I/O device, and the like.

The one or more program modules discussed herein carry out the methodologies disclosed herein. Flowcharts may illustrate architecture, functionality, and operation of possible implementations of systems, methods and computer program products according to various embodiments of the present invention. In this regard, each block in the flowchart may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently. It will also be noted that each block of flowchart illustration can be implemented by special purpose hardware-based systems that perform the specified functions or acts, or combinations of special purpose hardware and computer instructions.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method for lateral gaze angle estimation of a head of a user having two eyes using the determination of relative eye separation of the user, each eye having a pupil region, each pupil region having a substantial center, the method comprising:

finding the pupil region of each eye of the user from a video camera;

measuring an eye separation distance between the substantial centers of the pupil regions; and estimating the lateral gaze angle based upon the measured distance.

2. The method as defined in claim 1 further comprising determining a maximal eye separation distance.

3. The method as defined in claim 2 further comprising calculating a ratio of the measured eye separation distance to the maximal eye separation distance and calculating an inverse cosine value of the ratio and determining the lateral gaze angle based upon the calculated inverse cosine value.

4. The method as defined in claim 3 further comprising lighting up the pupil regions of the eyes of the user with infrared light using a first and a second set of infrared light emitting diodes, receiving and processing reflections of the infrared light from the eyes of the user.

5. The method as defined in claim 2 further comprising recording multiple measured eye separation distances over a period of time and determining the maximal eye separation distance by identifying the maximum measured eye separation distance from the multiple measured eye separation distances.

6. The method as defined in claim 1 finding the pupil of each eye of the user with a second camera, measuring a second eye separation distance between the substantial centers of the pupil regions from the second camera, and determining the lateral gaze angle based upon a comparison of the measured eye separation distance and the second measured eye separation distance.

7. A system for lateral gaze angle estimation of a head of a user having two eyes using the determination of relative eye separation of the user, each eye having a pupil region, the system comprising:

at least one video camera;

at least one processing unit;

a memory unit operably associated with the at least one processing unit;

a lateral gaze determination tool storable in the memory unit and executable by the at least one memory unit, the lateral gaze determination tool comprising:

a pupil region finding unit of each eye of the user in a video camera image from a video camera;

an eye separation distance measuring unit for measuring the separation distance between the substantial centers of the pupil regions; and a lateral gaze angle determining unit based upon the measured distance.

8. The system as defined in claim 7 wherein the eye separation distance measuring unit comprises a maximal eye separation distance determining unit.

9. The system as defined in claim 8 wherein the lateral gaze angle determining unit comprises a ratio calculating unit for calculating the ratio of the measured eye separation distance to the maximal eye separation distance and calculating an inverse cosine value of the ratio.

10. The system as defined in claim 9 wherein the lateral gaze angle determining unit is configured to calculate the lateral gaze angle based upon the calculated inverse cosine value.

11. The system as defined in claim 8 wherein the maximal eye separation distance determining unit is configured for recording multiple measured eye separation distances over a period of time and determining the maximal eye separation distance by identifying the maximum measured eye separation distance from the multiple measured eye separation distances.

12. The system as defined in claim 7 further comprising a second camera for finding the pupil of each eye of the user with a second camera, the eye separation distance measuring unit measuring a second eye separation distance between the substantial centers of the pupil regions from the second camera, and the lateral gaze angle determining unit determining the lateral gaze angle based upon a comparison of the measured eye separation distance and the second measured eye separation distance.

13. A computer program product embodied in a computer readable medium for operating in a system comprising a processing unit, a memory, a bus, and input/output (I/O) interfaces, for implementing a method for estimating lateral gaze angle of a head of a user having two eyes using the determination of relative eye separation, each eye having a pupil region, the method comprising:
   finding the pupil region of each eye of the user in a video camera image from a video camera;
   measuring an eye separation distance between the substantial centers of the pupil regions; and
   determining the lateral gaze angle based upon the measured distance.

14. The computer program product as defined in claim 13 wherein the method further comprises determining a maximal eye separation distance.

15. The computer program product as defined in claim 14 wherein the method further comprises calculating a ratio of the measured eye separation distance to the maximal eye separation distance and calculating an inverse cosine value of the ratio.

16. The computer program product as defined in claim 15 wherein the method further comprises determining the lateral gaze angle based upon the calculated inverse cosine value.

17. The computer program product as defined in claim 16 wherein the method further comprises recording multiple measured eye separation distances over a period of time and determining the maximal eye separation distance by identifying the maximum measured eye separation distance from the multiple measured eye separation distances.

18. A method for deploying computing infrastructure comprising integrating computer-readable code into a computing system, wherein the code in combination with the computing system is capable of performing a process for lateral gaze angle estimation of a head of a user having two eyes using the determination of relative eye separation of the user, each eye having a pupil region, the process comprising:
   finding the pupil region of each eye of the user in a video camera image from a video camera;
   measuring an eye separation distance between the substantial centers of the pupil regions; and
   determining the lateral gaze angle based upon the measured distance.

19. The method for deploying computing infrastructure comprising integrating computer-readable code into a computing system as defined in claim 18 wherein the process further comprises determining a maximal eye separation distance comprising recording multiple measured eye separation distances over a period of time and determining the maximal eye separation distance by identifying the maximum measured eye separation distance from the multiple measured eye separation distances.

20. The method for deploying computing infrastructure comprising integrating computer-readable code into a computing system as defined in claim 19 wherein the process further comprises calculating a ratio of the measured eye separation distance to the maximal eye separation distance and calculating an inverse cosine value of the ratio and further comprising determining the lateral gaze angle based upon the calculated inverse cosine value.

\* \* \* \* \*